United States Patent
Liu et al.

(10) Patent No.: US 10,488,533 B2
(45) Date of Patent: Nov. 26, 2019

(54) SYSTEM AND METHOD FOR COOLING IMAGING SYSTEM

(71) Applicant: SHANGHAI UNITED IMAGING HEALTHCARE CO., LTD., Shanghai (CN)

(72) Inventors: Weiping Liu, Shanghai (CN); Yixing Sun, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 651 days.

(21) Appl. No.: 15/175,785

(22) Filed: Jun. 7, 2016

(65) Prior Publication Data

US 2017/0176607 A1    Jun. 22, 2017

(30) Foreign Application Priority Data

Dec. 18, 2015    (CN) .......................... 2015 1 0958623

(51) Int. Cl.

| G01T 1/24 | (2006.01) |
|---|---|
| H01L 31/024 | (2014.01) |
| G01J 5/06 | (2006.01) |
| G01T 1/164 | (2006.01) |
| G01T 1/29 | (2006.01) |

(52) U.S. Cl.
CPC .............. *G01T 1/244* (2013.01); *G01J 5/061* (2013.01); *G01T 1/1648* (2013.01); *G01T 1/249* (2013.01); *G01T 1/2985* (2013.01); *H01L 31/024* (2013.01)

(58) Field of Classification Search
CPC ....... G01T 1/244; G01T 1/1648; G01T 1/249; G01T 1/2985; G01J 5/061; H01L 31/024; A61B 6/4488

USPC ....................................................... 250/363.03
See application file for complete search history.

(56) References Cited

U.S. PATENT DOCUMENTS

| 7,201,515 B2 | 4/2007 | Lacey |
|---|---|---|
| 9,086,360 B2 | 7/2015 | Joshi et al. |

(Continued)

FOREIGN PATENT DOCUMENTS

| CN | 103860187 B | 5/2015 |
|---|---|---|
| JP | H11128211 A | 5/1999 |
| JP | 2000037374 A | 2/2000 |

OTHER PUBLICATIONS

International search report in International Application No. PCT/CN2016/105373 dated Feb. 13, 2017, 5 pages.

(Continued)

*Primary Examiner* — David P Porta
*Assistant Examiner* — Abra S Fein
(74) *Attorney, Agent, or Firm* — Metis IP LLC

(57) ABSTRACT

An imaging system including an imaging device and/or a cooling system is provided. The imaging system may include a control module, an imaging device, and/or a cooling system. The imaging device may include a first portion and a second portion. The cooling system may include a cooling module configured to generate a cooling medium, and/or a cooling medium passage configured to spread the cooling medium. The cooling medium passage may belong to a closed loop. At least part of the cooling system may be located within the imaging device such that the cooling medium may be in direct contact with the at least part of the imaging device.

19 Claims, 12 Drawing Sheets

(56) References Cited

U.S. PATENT DOCUMENTS

| | | |
|---|---|---|
| 2003/0017051 A1* | 1/2003 | Coutandin ............ F01D 5/187 416/97 R |
| 2003/0021676 A1* | 1/2003 | Tiemann ................ F01D 5/22 415/134 |
| 2005/0117698 A1 | 6/2005 | Lacey et al. |
| 2007/0080296 A1 | 4/2007 | Ueno et al. |
| 2010/0266096 A1 | 10/2010 | Sharpless |
| 2013/0119259 A1 | 5/2013 | Martin |
| 2015/0182183 A1 | 7/2015 | Ergler et al. |
| 2017/0176607 A1 | 6/2017 | Liu et al. |

OTHER PUBLICATIONS

Written opinion in International Application No. PCT/CN2016/105373 dated Feb. 13, 2017, 5 pages.

* cited by examiner

SYSTEM AND METHOD FOR COOLING IMAGING SYSTEM

CROSS-REFERENCE TO RELATED APPLICATIONS

This application claims priority of Chinese Application No. 201510958623.4 filed on Dec. 18, 2015, the entire contents of which are hereby incorporated herein by reference.

TECHNICAL FIELD

This application relates generally to cooling components of an imaging system. More particularly, this application relates to cooling components of an imaging system having a gantry housing.

BACKGROUND

An imaging device such as a computed tomography (CT), a magnetic resonance imaging (MRI) system, a single-photon emission computed tomography (SPECT), or a positron emission tomography (PET) system is used for diagnosis and other purposes. Positron emission tomography (PET) may apply a radiology procedure that may be used to evaluate the physiology (functionality) and anatomy (structure) of a target organ or tissue, as well as its biochemical properties. Changes in these properties of the target organ or tissue may provide information for the identification of the onset of a disease process.

A PET scanner may contain temperature-sensitive components and thus need a cooling system to maintain a suitable working temperature. Additionally, optimal functionality of a PET scanner may also rely on precise coupling and communication between its optical components and electrical components. Thus, there exists a need to provide a cooling system for a PET scanner that may overcome these and other technical challenges.

SUMMARY

The present disclosure relates to an imaging system based on an imaging device and/or a cooling system. The imaging system may include a control module, an imaging device, and/or a cooling system. The imaging device may include a first portion and a second portion. The cooling system may include a cooling module configured to generate a cooling medium, and/or a cooling medium passage configured to spread the cooling medium. In some embodiments, the cooling medium passage may belong to a closed loop. In some embodiments, at least part of the cooling system may be located within the imaging device such that the cooling medium may be in direct contact with the at least part of the imaging device.

In some embodiments, the cooling medium passage may include a first sub-passage and a second sub-passage, the first sub-passage may be located within the first portion, and the second sub-passage may be located within the second portion.

In some embodiments, at least part of the first sub-passage may be configured to form a fluid communication between the first portion and the second portion.

In some embodiments, the second portion may include a detector unit.

In some embodiments, at least a portion of the detector unit may be located within the second sub-passage.

In some embodiments, the cooling medium may contact the detector unit.

In some embodiments, the second portion may further include an electronics unit.

In some embodiments, at least a portion of the detector unit and the electronics unit may be located within the second sub-passage.

In some embodiments, the cooling medium may contact the detector unit and the electronics unit.

In some embodiments, the second portion may further include a first plate, and the first plate may divide the second portion into a first chamber and a second chamber in fluid communication with the first chamber.

In some embodiments, the first plate and the detector unit may divide the second portion into three chambers.

In some embodiments, the cooling system may further include a temperature control module.

In some embodiments, the temperature control module may include a temperature detector.

In some embodiments, the cooling module may include fan and a heat exchanger.

In some embodiments, the imaging device may be a Positron Emission Tomography (PET) device.

In some embodiments, the cooling system may further include a peripheral cooling medium passage.

BRIEF DESCRIPTION OF THE DRAWINGS

The present disclosure is further described in terms of exemplary embodiments. These exemplary embodiments are described in detail with reference to the drawings. These embodiments are non-limiting examples, in which like reference numerals represent similar structures throughout the several views of the drawings, and wherein.

DETAILED DESCRIPTION

Figure 1:
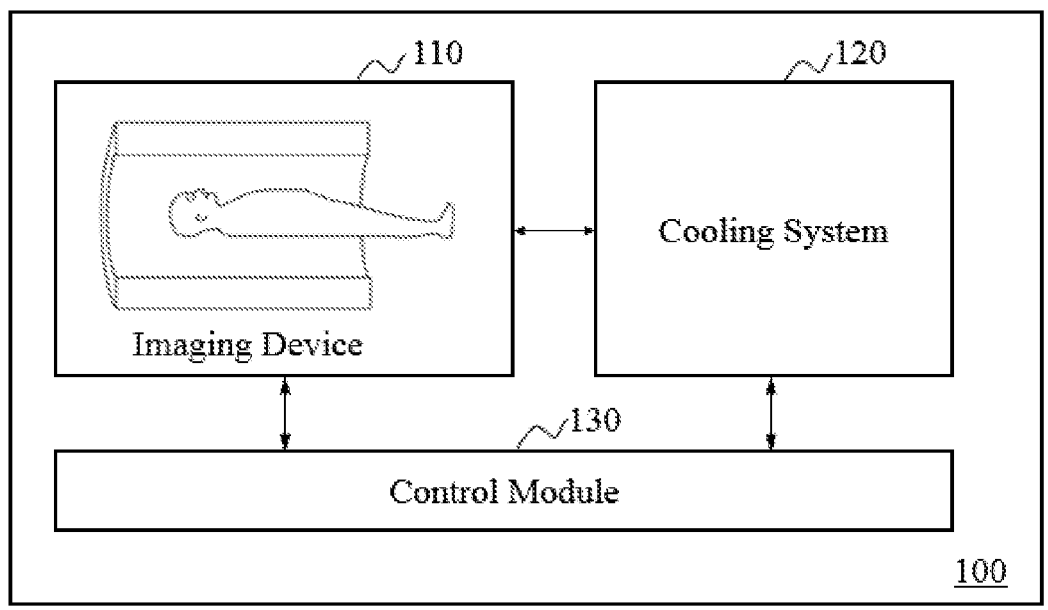
FIG. 1 is a block diagram illustrating an imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry include been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "unit," "module," and/or "block" used herein are one method to distinguish different components, elements, parts, section or assembly of different level in ascending order. However, the terms may be displaced by other expression if they may achieve the same purpose.

It will be further understood that the term "plate," "clapboard," "bulkhead," and/or "baffle" when used in this disclosure, specify to divide a system, a module, a unit or a block into at least two compartments or chambers, unless the context clearly indicates otherwise. However, the terms may be displaced by other expression if they may achieve the same purpose.

It will be understood that when a unit, engine, module or block is referred to as being "on," "connected to" or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

Provided herein are systems and components for non-invasive biomedical imaging, such as for disease diagnostic or research purposes. The system may include a single imaging modality or multiple imaging modalities for conducting different medical scans or studies, including but not limited to ultrasound scan, X-ray scan, bone densitometry, fluoroscopy, computed tomography (CT), digital radiography (DR), single photon emission computed tomography (SPECT), magnetic resonance imaging (MRI), positron emission tomography (PET) or the like, or any combination thereof.

The term "imaging modality" or "modality" as used herein broadly refers to an imaging method or technology that gathers, generates, processes and/or analyzes imaging information of a target body through a particular mechanism. The term "target body" or "object" as used herein broadly relates to any organic or inorganic mass, natural or man-made to be imaged or examined. Exemplary embodiments of a target body pertaining to the present disclosure include cells, tissues, organs or whole bodies of human or animal. Other exemplary embodiments of a target body include but not limited to a man-made composition of organic and/or inorganic matters that are with or without life.

Accordingly, a multi-modality imaging system of the present disclosure can include more than one imaging modality, such as two, three, or more different modalities. In a multi-modality system, the mechanisms through which different imaging modalities operate or function may be the same or different. Accordingly, the imaging information may also be the same or different. For example, in some embodiments, the imaging information may be internal and/or external information, functional and/or structural information of the target body, or the like, or a combination thereof. In some embodiments, the imaging information of different modalities may complement one another, thereby providing a set of imaging data describing a target body. For example, in some embodiments, the multi-modality imaging may achieve the merging of morphological and functional images.

The above types of imaging modalities that may be included in the present system are not exhaustive and are not limiting. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

FIG. 1 is a block diagram illustrating an imaging system according to some embodiments of the present disclosure. An imaging system 100 may generate an image of an object. The object may include a biological object and non-biological object. The biological object may be a human being, an animal, a plant or any other objects including cells, tissues, and organs. In some embodiments, the object may be a man-made composition of organic and/or inorganic matters that are with or without life. As illustrated, the imaging system 100 may include an imaging device 110, a cooling system 120, and a control module 130.

The imaging device 110 may scan an object, generate a plurality of data relating to the object. The imaging device 110 may further reconstruct an image from the plurality of data. In some embodiments, the imaging device 110 may be a medical imaging device, for example, a PET device, a SPECT device, a CT device, an MRI device, or the like, or any combination thereof (e.g., a PET-CT device, a PET-MRI device, or a SPECT-MRI device). In some embodiments, the imaging device 110 may include a gantry. Different imaging devices may use different detection principles and apply different configurations. Merely by way of example, for imaging using a PET device, molecules carrying radioactive tracers (e.g., positron radionuclide labeled glucose or other metabolites) may be first introduced to an object, then gamma rays emitted by the tracers may be detected and an image reflecting the tracer concentration distribution within the object may be generated. To be illustrative, a PET device may include a scintillator, a photodetector, and a set of electronics. The scintillator may absorb ionizing radiation and emit a fraction of the absorbed energy as light. The photodetector may sense the light pulses emitted from the scintillator and convert them into an electrical signal. The set of electronics may collect and/or process the electrical signal. In some embodiments, the set of electronics may be a frontend one. A frontend electronics may be operably connected to the scintillator. In some embodiments, the frontend electronics may include an amplifier, a filter, and/or an analog-to-digital converter. In some embodiments, the frontend electronics may collect the electrical signals, perform signal conditioning, and/or output digital signals. In some embodiments, the frontend electronics may be different from a backend electronics that is not operably connected to the scintillator. In some embodiments, the backend electronics may further process and/or analyze the digital signals generated by the frontend electronics. As another example, a CT device may include an X-ray generator generating X-rays to traverse an object under examination, and an X-ray detector receiving the X-rays and generating raw data of an X-ray image. As a further example, an MRI device may include magnet field generators creating a static magnetic field and magnet field gradients, and RF coils transmitting RF signals to or receiving RF signals from an object examined. Generally, the imaging device 110 may include a detector unit collecting signals (e.g., ionizing radiation, photon, X-ray, RF signals, electrical signals, or the like, or any combination thereof) from an object, an electronics unit (e.g., frontend electronics, backend electronics, various amplifiers, filters, and analog-to-digital converters, or the like, or any combination thereof) collecting and processing electrical signals, and other peripheral units (e.g., an input/output, a display, a storage, a printer, or the like, or any combination thereof). The imaging device 110 may include a first portion and a second portion. For instance, the second portion may refer to a portion containing a detector unit or/and an electronics unit. The first portion may refer to a portion excluding the detector unit. In some embodiments, the imaging device 110 may include a gantry and a gantry housing (e.g. those illustrated in FIG. 3). In some embodiments, the second portion may be located in the gantry housing. In some embodiments, at least part of the first portion may be located in the gantry housing.

The cooling system 120 may produce, transfer, deliver, channel, or circulate a cooling medium to the imaging device 110 to absorb heat produced by the imaging device 110 during an imaging procedure. In some embodiments, the cooling system 120 may be entirely integrated into the imaging device 110 and become a part of the imaging device 110. In some embodiments, the cooling system 120 may be partially integrated into the imaging device 110 and associated with the imaging device 110. The cooling system 120 may allow the imaging device 110 to maintain a suitable and stable working temperature. In some embodiments, the cooling system 120 may control the temperature at one or more target locations of the imaging device 110. The target location may include a detector unit, an electronics unit and/or any other unit with heat emission. The cooling medium may be gaseous, liquid (e.g., water), or the like, or any combination thereof. In some embodiments, the gaseous cooling medium may be air. Exemplary gaseous cooling media may include an inert gas, nitrogen, carbon dioxide, or the like, or a combination thereof.

The control module 130 may control the imaging device 110 and the cooling system 120. The control module 130 may receive signals or instructions from or send information to the imaging device 110, the cooling system 120, and/or other modules or units in the imaging system 100. In some embodiments, the control module 130 may include or provide a computer, a program, an algorithm, a software, a storage device, one or more interfaces, etc. Exemplary interfaces may include the interfaces of the imaging device 110, the cooling system 120, and/or other modules or units in the imaging system 100. In some embodiments, the control module 130 may receive instructions from peripheral units (e.g., an input/output) provided by a user, and send commands to the imaging device 110 and the cooling system 120. In some embodiments, the control module 130 may control a data storage of the imaging system 100. For instance, the control module 130 may control the location of data storage, the content of data storage, the method of data storage, the indexing of the stored data, or the like, or a combination thereof.

Figure 2:
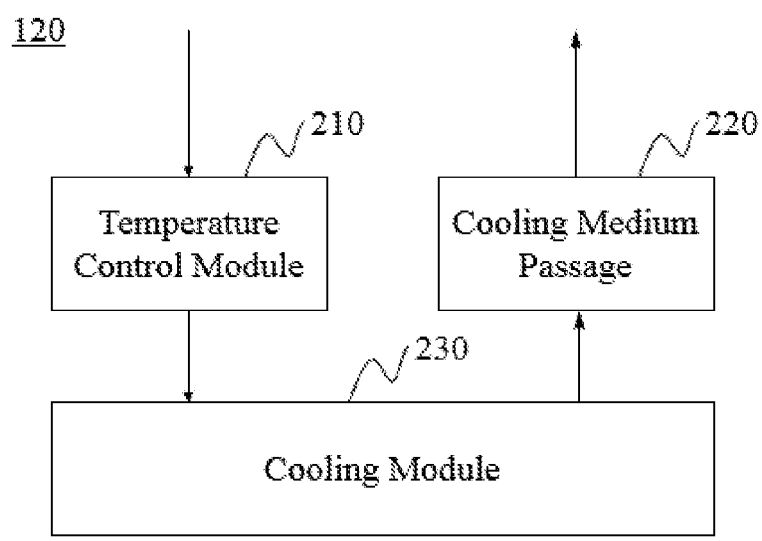
FIG. 2 is a block diagram illustrating a cooling system according to some embodiments of the present disclosure.

FIG. 2 is a block diagram illustrating a cooling system according to some embodiments of the present disclosure. The cooling system 120 may include a temperature control module 210, a cooling medium passage 220, and a cooling module 230.

The cooling module 230 may be configured to generate and deliver cooling medium. The cooling medium generated may be a cooling gas (e.g., air), or a cooling fluid (e.g., water, or coolant). In some embodiments, the cooling module 230 may be located within the first portion. The cooling medium may absorb heat from the imaging device 110. In some embodiments, the heat-laden cooling medium may be discharged and fresh cooling medium may be replenished to the cooling system 120. In some embodiments, the heat-laden cooling medium may be cooled by the cooling module. The cooling module 230 may include a cooling apparatus, a heat exchanger, and a distribution unit. The cooling apparatus may be configured to absorb heat from the cooling medium. In some embodiments, the cooling apparatus may dissipate the absorbed heat to the ambient. The cooling apparatus may be thermally coupled with the heat exchanger.

The heat exchanger may be configured to exchange heat with the cooling medium. Merely by way of example, after absorbing heat from the imaging device, the heat-laden cooling medium may transfer the heat to the cooling apparatus through the heat exchanger. In some embodiments, the heat-laden cooling medium may be cooled by the cooling apparatus through the heat exchanger. In some embodiments, the heat transfer and the cooling of the heat-laden cooling medium may be carried out at the same time. In some embodiments, the cooling of the heat-laden cooling medium may be carried out in a time delay. As another example, fresh cooling medium may need to be replenished to the cooling system 120. The fresh cooling medium may be initially at the room temperature and may need to be cooled by the cooling apparatus. In some embodiments, the cooling apparatus may include a cryogen. The cryogen may absorb heat from a cooling medium through the heat exchanger. The cooling apparatus may also include mechanisms to cool the cryogen, and/or recycle the cryogen. The distribution unit may deliver the cooling medium to one or more target locations of the imaging system 110. The distribution unit may include a driver or mover to drive the cooling medium into different cooling medium passages 220. For example, when a gaseous cooling medium is used, the distribution unit may be a fan or a blower.

The cooling medium passage 220 may be configured to channel the cooling medium to one or more target locations of the imaging device 110. Any unit of the imaging device 110 including, for example, the detector unit, the electronics unit, or any other peripheral unit, etc., may include a cooling medium passage 220. The cooling medium passage 220 of a unit may be located inside, outside, or near a specific unit or an interspace between units. In some embodiments, at least some cooling medium passages 220 of different units of the imaging device 110 may be isolated or disconnected from each other, or in fluid communication or connected with each other. In some embodiments, a cooling medium passage 220 of a first unit may be isolated or disconnected from the cooling medium passage 220 of a second unit, and in fluid communication with the cooling unit of a third unit. In some embodiments, some of the cooling medium passages 220 may form a closed loop (e.g. the cooling medium may circulate within the passages).

As used herein, a closed loop or a closed space refers to a loop or space that is continuous, and does not exchange mass (e.g., a gas, a liquid, a solid) with the outside of the closed loop or space (at least by design and except for, for example, leakage due to a defect of the loop or space). A closed loop or a closed space may include an opening that may be opened to allow mass exchange between the loop or space and the outside. When the opening is opened, the loop or space is not a closed one; when the opening is closed, the loop or space is a closed one. Without mass exchange, a closed loop or a closed space may exchange, with the outside, energy in the form of, for example, heat, electromagnetic energy, acoustic energy, or the like, or a combination thereof.

In some embodiments, some of the cooling medium passages 220 may be connected with the ambient of the imaging device 110. Merely by way of example, all the cooling medium passages 220 may be connected with each other, and form at least part of a closed loop. As another example, the cooling medium passages 220 of the detector unit may be connected with each other, and belong to a closed loop. As a further example, the cooling medium passages 220 of the electronics unit may be connected with each other, and at least one of these cooling medium passages 220 may be further open to the ambient of the imaging device 110. As still a further example, the cooling medium passages 220 of the detector unit and the electronics unit may be connected with each other, and form at least part of a closed loop. In some embodiments, one or more components of the cooling module 230 may form part of a closed loop including the cooling medium passages 220. Such components may include a heat exchanger, a distribution unit, or the like, or any combination thereof.

The temperature control module 210 may be configured to control the operation of the cooling module 230. The temperature control module 210 may include a temperature detection unit, a temperature controller, or the like, or any combination thereof. The temperature detection unit may be used to monitor the temperature of a target location of, for example, the imaging device 110. The temperature detection unit may further include at least one temperature sensor. In some embodiments, there may be a plurality of temperature sensors distributed in the imaging system 100. The temperature control module 210 may control the working condition of the cooling apparatus in the cooling module 230, for example, the ON/OFF state, the cooling frequency, the flow rate of the cryogen, or the like, or a combination thereof. Different distribution units located at different positions may be controlled independently. In some embodiments, the temperature control module 210 may implement control according to the temperature sensed by one or more temperature sensors.

It should be noted that the above description of the diagram in FIG. 2 is merely provided for the purposes of illustration, and not intended to limit the scope of the present disclosure. For persons having ordinary skills in the art, multiple variations or modifications may be made under the teachings of the present disclosure. For example, the temperature control module 210 may be unnecessary, or the temperature control may be carried out automatically. As another example, the temperature control module 210 may be integrated into the control module 130 of the imaging system 100. As another example, the temperature control module 210 may further include a temperature controller to implement control based on the temperature detection unit.

Figure 3:
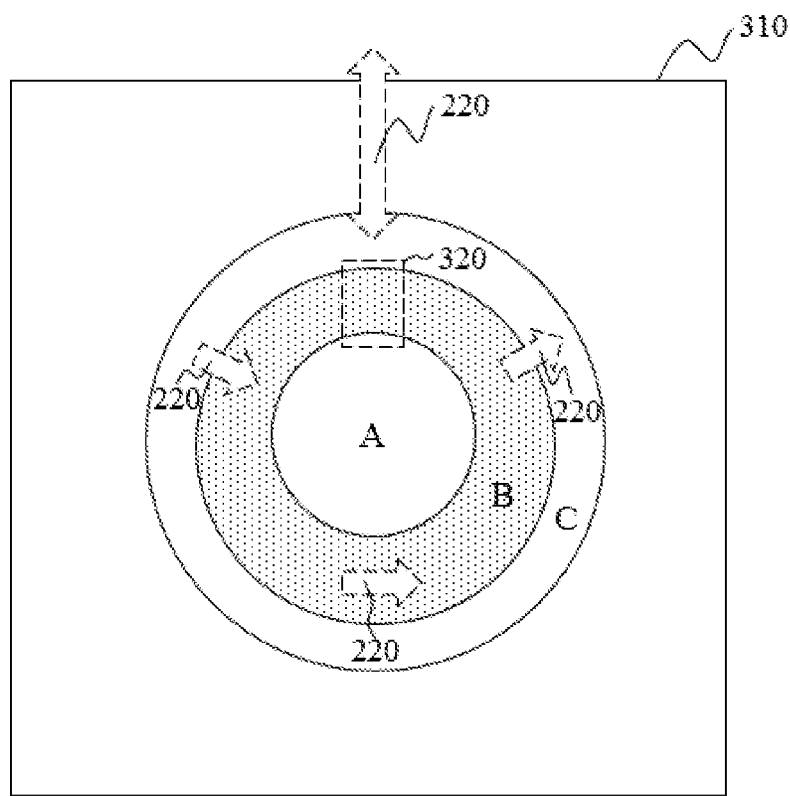
FIG. 3 is a schematic diagram illustrating the configuration of an exemplary cooling medium passage in an imaging system according to some embodiments of the present disclosure.

FIG. 3 is a schematic diagram illustrating the configuration of the cooling medium passage 220 in the imaging system 100 according to some embodiments of the present disclosure. The imaging system 100 may include an imaging device gantry 310. The imaging device gantry 310 may refer to a gantry of an imaging device 110. The imaging device gantry 310 may include region A, region B, and region C. Region A may be a gantry aperture, or an examination space to place an object for scanning or examination. Region B may refer to a gantry housing. The gantry housing may house a detector unit and/or an electronics unit. For example, region B may include a scintillator, a photodetector, and/or a set of frontend electronics of a PET device. Region C may refer to a space between the gantry housing and the gantry (for example, as a peripheral cooling medium passage 810 illustrated in FIG. 8A). In some embodiments, Region C may be unnecessary. In some embodiments, Region C may include a detector different from that in region B. Merely by way of example, in a PET-MRI hybrid system, region C may include an MRI coil, while region B may include a PET detector, or vice versa. As another example, in a hybrid system, the imaging device gantry 310 may include an X-ray detector, a PET detector, or any other detector receiving signals, or any combination thereof. The cooling medium passage 220 may be distributed within region B, region C, or anywhere else inside the imaging device gantry 310. Exemplary configurations of the cooling medium passage 220 within region B are illustrated in FIG. 4 and described elsewhere in the present disclosure.

In some embodiments, the gantry housing may be a closed space. The cooling medium passage 220 inside region B may form a closed loop. Region B and region C may be isolated from each other and lack fluid communication. In some embodiments, region B and region C may be in fluid communication via, for example, a cooling medium passage 220; a cooling medium may be delivered from region B to region C, and/or from region C to region B. For example, region B may include an inlet/outlet (e.g., one or more ventilation holes) for the cooling medium flow between region B and region C. In some embodiments, the cooling medium passage 220 inside region C may be connected with that of the imaging device gantry 310 and further connected to the ambient of the imaging device gantry 310. For example, when a gaseous cooling medium is used, the cooling medium may be imported from the ambient of the imaging device gantry 310, and flow through the cooling medium passage 220 in region C, and/or region B, and then output to the ambient of the imaging device gantry 310. In some embodiments, at least part of the cooling medium passage 220 in the imaging device gantry 310 may form a closed loop, which means the cooling medium may be circulated in the gantry without connecting or contacting the ambient of the gantry.

FIGS. 4A through 4D illustrate exemplary cooling medium passages 220 within the gantry housing 320 of an imaging system according to some embodiments of the present disclosure. The cooling medium passage 220 may be set near the detector unit 430, and/or the electronics unit 440. In some embodiments, the cooling medium in the cooling medium passage 220 may contact the detector unit 430, and/or the electronics unit 440. For instance, a gaseous cooling medium may contact the detector unit 430, and/or the electronics unit 440.

The detector unit 430 may collect signals (e.g., ionizing radiation, photon, X-ray, RF signals, electrical signals, or the like, or any combination thereof) from an object. Merely by way of example, for a PET device, the detector unit 430 may include a scintillator and/or a photodetector. As another example, for a CT device, the detector unit 430 may include an X-ray detector. As a further example, for an MRI device, the detector unit 430 may include RF coils. As a still further example, for a PET-CT hybrid system, the detector unit 430 may include a scintillator, a photodetector, and/or an X-ray detector. The electronics unit 440 may collect and/or process electrical signals. In some embodiments, the electronics unit 440 may include a printed circuit board (PCB), a flexible printed circuit board (FPCB), or the like, or any combination thereof. The circuit board may include an amplifier, a filter, an analog-to-digital converter, a capacitor, a resistor, an inductor, or the like, or any combination thereof.

In some embodiments, the detector unit and the electronics unit may be located in the gantry housing 320. The location may be between the inner sidewall 420 of the gantry housing 310 and the outer sidewall 410 of the gantry housing 310 (e.g. that illustrated in FIGS. 4A, 4C, and 4D). In some embodiments, the detector unit 430 may be placed within the gantry housing 320, while the electronics unit 470 may be placed outside the gantry housing 320 in, for example, region C (e.g. that illustrated in FIG. 4B). In some embodiments, the cooling medium passage 220 within the gantry housing 320 may be in fluid communication or connected with a region, e.g., region C, outside the outer sidewall 410 of the gantry housing 320. The connection may be realized through an inlet/outlet 460 on the outer sidewall 410 of the gantry housing 320 and/or the inner sidewall 420 of the gantry housing 320. When a gaseous cooling medium is used, the inlet/outlet 460 may take the form of a ventilation hole.

In some embodiments, the cooling medium passage 220 within the gantry housing 320 may form or be part of a closed loop. For example, the inner sidewall 420 of the gantry housing 310 and/or the outer sidewall 410 of the gantry housing 310 may include no inlet/outlet 460. In some embodiments, the cooling medium passage 220, along with a distribution unit and/or a heat exchanger, may form a closed loop. In some embodiments, the entire closed loop may be located within the gantry housing 320. For example, the cooling medium passage 220, the distribution unit, and/or the heat exchanger may be all located within the gantry housing 320. In some embodiments, part of the closed loop may be located within the gantry housing 320. For example, a closed loop may include the cooling medium passage 220, the distribution unit, and/or the heat exchanger; part of the closed loop, e.g., the cooling medium passage 220 may be located within the gantry housing 320; part of the closed loop including the cooling medium passage 220, the distribution unit, and/or the heat exchanger may be located outside the gantry housing.

Figure 4A:
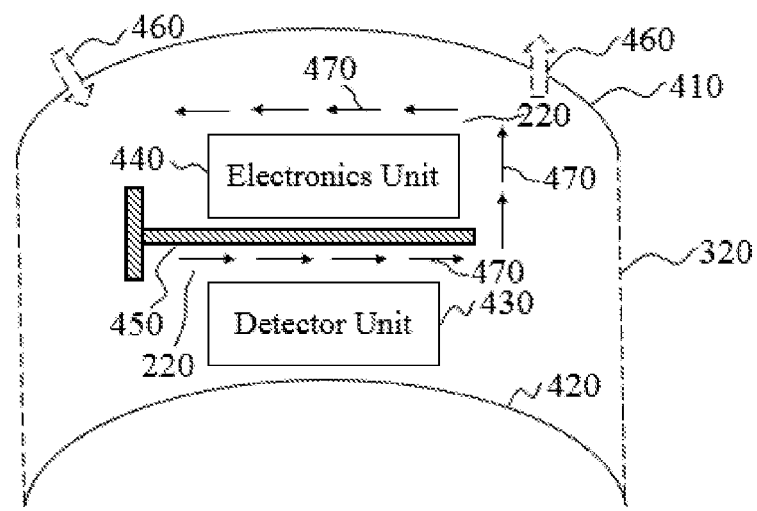
FIGS. 4A through 4D illustrate exemplary cooling medium passages within the gantry housing of an imaging system according to some embodiments of the present disclosure.

FIG. 4A shows an exemplary configuration of the cooling medium passage 220 for a detector unit 430 and an electronics unit 440 in the gantry housing 320. At least one bulkhead 450 may be located between or close to the detector unit 430 and the electronics unit 440. In some embodiments, the bulkhead 450 do not completely block the cooling medium passage 220 between the detector unit 430 and the electronics unit 440. For example, one or more ventilation holes (not shown) may be set on the bulkhead 450, allowing a cooling medium to flow from the vicinity of the detector unit 430 to the vicinity of the electronics unit 440, as illustrated by the arrows 470. The arrows 470 may illustrate the direction of a bulk flow of the cooling medium in the cooling medium passage 220, rather than the exact flow direction of the cooling medium. In some embodiments, the gantry housing 320 may house at least a part of the cooling module 230 (see, for example, FIG. 9 in which a compressor of the cooling module 230 is located outside of the gantry housing 320). For example, the part of the cooling module 230 located inside the gantry housing 320 may channel the cooling medium to move in one direction. In some embodiments, the cooling medium passage 220 may also be located in some other parts of the gantry housing 320. In some embodiments, the bulkhead 450 may completely block the cooling medium passage 220 between the detector unit 430 and the electronics unit 440.

Figure 4B:
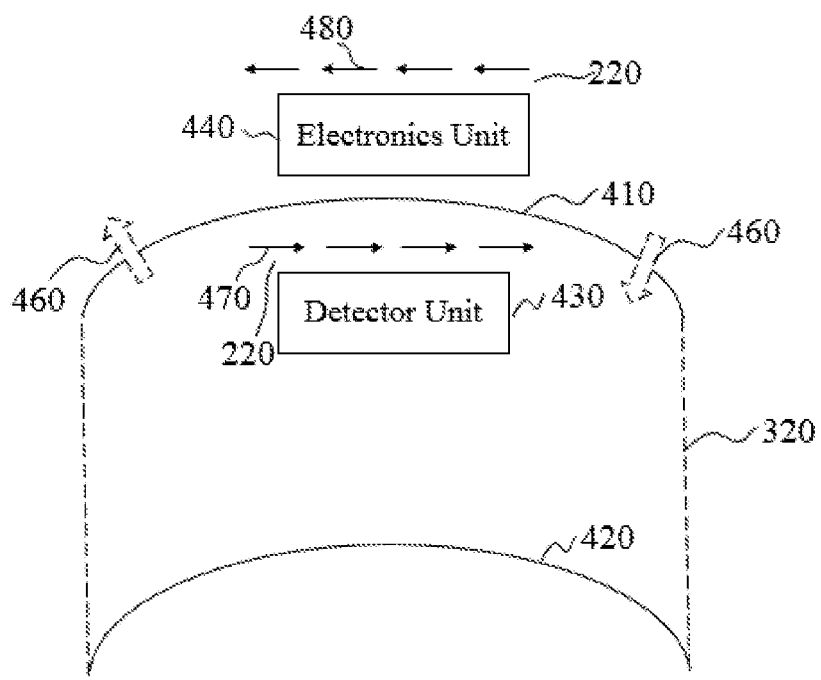

FIG. 4B shows an exemplary configuration of the cooling medium passage 220 for a detector unit 430 and an electronics unit 440 in the gantry housing 320. The detector unit 430 may be placed in the gantry housing 320, while the electronics unit 440 may be placed outside the gantry housing 320. In some embodiments, the cooling medium passage 220 between the detector unit 430 and the electronics unit 440 may be separated by the outer sidewall 410 of the gantry housing 320. The cooling medium passage 220 for the detector unit 430 may form part of a closed loop, allowing the cooling medium flow through the vicinity of the detector unit 430, as illustrated by the arrows 470. In some embodiments, a distribution unit and/or a heat exchanger may be part of the closed loop. The cooling medium passage 220 for the electronics unit 440 may form another closed loop, or connect to other cooling medium passages 220 isolated from the cooling medium passage 220 for the detector unit 430, allowing another cooling medium to flow through the vicinity of the electronics unit 440, as illustrated by the arrows 480. In some embodiments, the cooling medium passage 220 between the detector unit 430 and the electronics unit 440 may be connected or in fluid communication through an inlet/outlet 460 on the outer sidewall 410 of the gantry housing 320. For example, the cooling medium may flow from the vicinity of the detector unit 430 (as illustrated by arrows 470), through one or more ventilation holes as indicated by an inlet/outlet 460, to the vicinity of the electronics unit 440 (as illustrated by arrows 480). The arrows 470 and 480 may illustrate the direction of a bulk flow of the cooling medium in the cooling medium passage 220, rather than the exact flow direction of the cooling medium. In some embodiments, the gantry housing 320 may house at least a part of the cooling module 230 (see, for example, FIG. 9 in which a compressor of the cooling module 230 is located outside of the gantry housing 320). For example, the part of the cooling module 230 located inside the gantry housing 320 may channel the cooling medium to move in one direction.

Figure 4C:
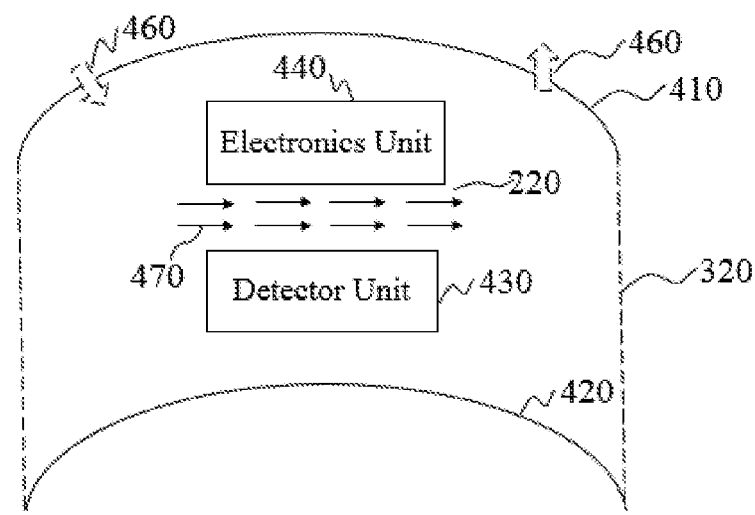

FIG. 4C shows another exemplary configuration of a cooling medium passage 220 for a detector unit 430 and an electronics unit 440 in a gantry housing 320. The detector 430 may be in the vicinity of the electronics unit 440. A cooling medium passage 220 may be located between and/or close to the detector 430 and the electronics unit 440. For example, the cooling medium may flow through the vicinity the detector 430 and the electronics unit 440 at the same time, as illustrated by the arrows 470. The arrows 470 may illustrate the direction of a bulk flow of the cooling medium in the cooling medium passage 220, rather than the exact flow direction of the cooling medium. In some embodiments, the cooling medium passage 220 between the detector unit 430 and the electronics unit 440 may form at least part of a closed loop. In some embodiments, the cooling medium passage 220 may connect to other cooling medium passages 220 outside the gantry housing through an inlet/ outlet 460 located on the outer sidewall 410 of the gantry housing 320. In some embodiments, the gantry housing 320 may house at least a part of the cooling module 230 (see, for example, FIG. 9 in which a compressor of the cooling module 230 is located outside of the gantry housing 320). For example, the part of the cooling module 230 located inside the gantry housing 320 may channel the cooling medium to move in one direction.

Figure 4D:
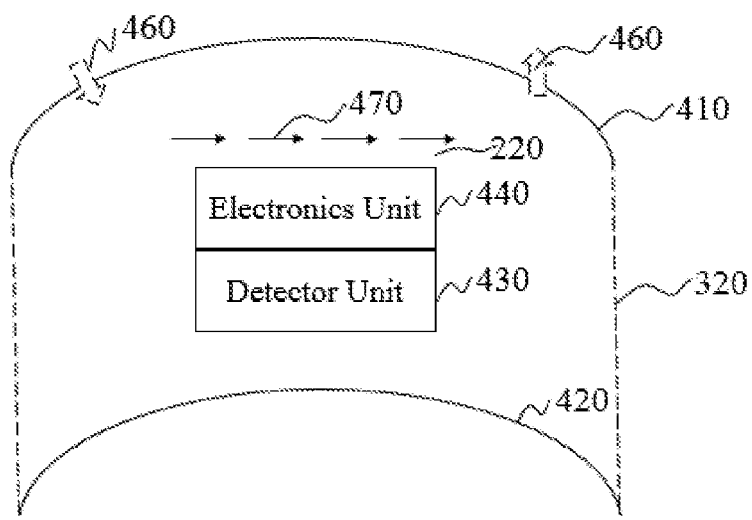

FIG. 4D shows another exemplary configuration of a cooling medium passage 220 for a detector unit 430 and an electronics unit 440 in a gantry housing 320. The detector unit 430 and the electronics unit 440 may be integrated into one unit. A cooling medium passage 220 may be located around, near, along or through the integrated unit, allowing the cooling medium to flow to the vicinity of the detector unit 430 and/or the electronics unit 440, as illustrated by the arrows 470. The arrows 470 may illustrate the direction of a bulk flow of the cooling medium in the cooling medium passage 220, rather than the exact flow direction of the cooling medium. In some embodiments, the cooling medium passage 220 for the integrated unit may form a closed loop. In some embodiments, the cooling medium passage 220 for the integrated unit may connect to or be in fluid communication with other cooling medium passages 220 outside the gantry housing 320 through an inlet/outlet 460 set on the outer sidewall 410 of the gantry housing 320. In some embodiments, the gantry housing 320 may house at least a part of the cooling module 230 (see, for example, FIG. 9 in which a compressor of the cooling module 230 is located outside of the gantry housing 320). For example, the part of the cooling module 230 located inside the gantry housing 320 may channel the cooling medium to move in one direction.

Figure 5:
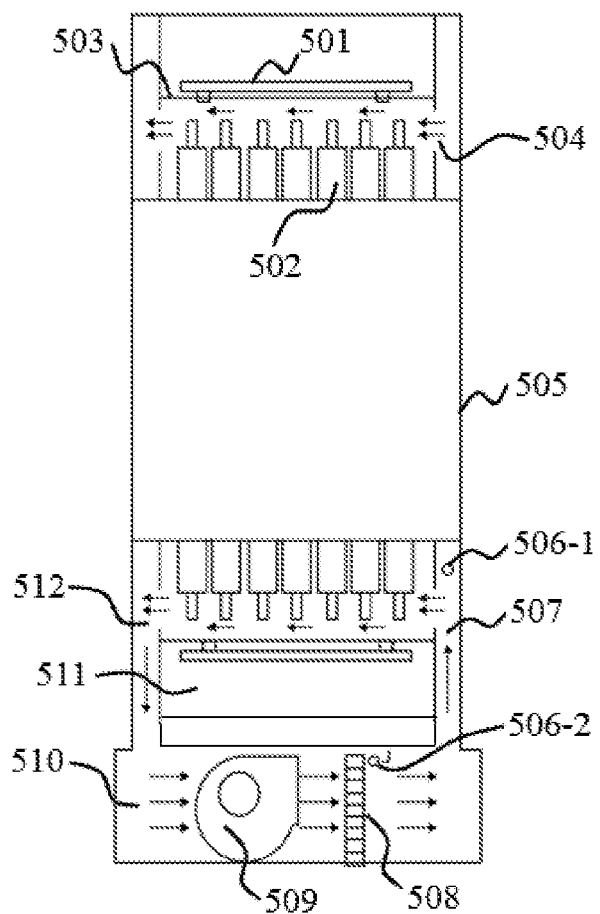
FIG. 5 is a schematic diagram illustrating an exemplary cooling medium passage according to some embodiments of the present disclosure.

FIG. 5 is a schematic diagram illustrating an exemplary cooling medium passage according to some embodiments of the present disclosure. The cooling medium passage may form at least part of a closed loop. The closed loop including the cooling medium passage may be located within an inner cavity of an imaging device gantry 505, for example, in a gantry housing. In some embodiments, the inner cavity may refer to a closed gantry housing. The closed loop including the cooling medium passage may include a distribution unit 509, a heat exchanger 508, and an inner cavity cooling medium passage 510. In some embodiments, the distribution unit 509 and/or the heat exchanger 508 may be located in the first portion of the imaging device. The distribution unit 509 may drive the cooling medium in the inner cavity cooling medium passage 510 to spread and/or circulate within the cavity of the inner cavity cooling medium passage 510. The distribution unit 509 may regulate the flow rate of the cooling medium. The distribution unit 509 may include a driver or a mover. For example, when a gaseous cooling medium is used, the distribution unit 509 may be a fan or a blower. In some embodiments, the flow rate of the cooling medium may be regulated through the variation of the rotation speed of the fan or the blower. The heat exchanger 508 may cool the cooling medium in the inner cavity. The heat exchanger 508 may be a shell and tube heat exchanger, a pillow plate heat exchanger, a fluid heat exchanger, a dynamic scraped surface heat exchanger, a phase-change heat exchanger, a direct contact heat exchanger, or the like, or any combination thereof. In some embodiments, the heat exchanger 508 may use a cryogen and/or a refrigerant to cool the cooling medium. The cryogen may include one or more substances with low temperature, for example, liquid gas (e.g., nitrogen, argon, krypton), an inorganic compound (e.g., liquid ammonia, water), or the like, or any combination thereof. The refrigerant may include freon, an azeotropic mixture, a hydrocarbon refrigerant, or the like, or any combination thereof. For example, the heat exchanger 508 may be an evaporator.

The arrows illustrated in FIG. 5 may indicate the inner cavity cooling medium passage 510. To be illustrative, the inner cavity cooling medium passage 510 may include an intake passage 507, a return passage 512, and other passages near the target locations in the inner cavity of the imaging device gantry 505. The intake passage 507 may guide a cooling medium cooled by the heat exchanger 508 toward target locations in the inner cavity. The cooled cooling medium may absorb heat from the target locations. The return passage 512 may guide the heat-laden cooling medium to return to the heat exchanger 508 to be cooled again. In some embodiments, an imaging device gantry 505 may include a first portion and a second portion. A cooling module may be located within the first portion. The second portion may refer to a portion containing a detector unit 502. The cooling medium passage in the first portion may be referred to as a first sub-passage. The cooling medium passage in the second portion may be referred to as a second sub-passage. The first sub-passage may include the intake passage 507 and the return passage 512. The second sub-passage may include the local passages close to the detector unit 502. In some embodiments, part of the second sub-passage may be alongside the detector unit 502. In some embodiments, a detector unit 502 may be placed in the inner cavity of the imaging device gantry 505, and the detector unit 502 may be the target location to be cooled. Part of the second sub-passages may be located close to the detector unit 502, as illustrated by the arrows around the detector unit 502. In some embodiments, when a gaseous cooling medium is used, the cooling medium in local passages may contact with the detector unit 502. For example, the detector unit 502 may be placed between the intake passage 507 and the return passage 512, and the cooling medium from the intake passage 507 may flow into the local passages near the detector unit 502. The cooling medium may further absorb heat of the detector unit 502 and/or flow to the return passage 512 to be cooled. In some embodiments, an electronics unit 501 may be placed outside the inner cavity. A plate 503 may be further set between the electronics unit 501 and the inner cavity. Thus, the inner cavity cooling medium passage 510 may form a closed loop. In some embodiments, a peripheral cooling medium passage 511 instead of the inner cavity cooling medium passage 510 may be located near the electronics unit 501.

In some embodiments, a plurality of temperature detectors 506 may be set in the inner cavity. The temperature detectors 506 may be placed at any location of the inner cavity cooling medium passage 510, including the intake passage 507, the return passage 512, and the local passages. For example, a temperature detector 506-1 may be placed near the detector unit 502 to monitor the temperature around the detector unit. As another example, a temperature detector 506-2 may be placed near the heat exchanger 508 to monitor the temperature of the cooling medium after cooling. The detected temperature may be recorded by the temperature control module 210, or the control module 130 of the imaging system 110, as shown in FIGS. 1 and 2. The temperature control module 210, and/or the control module 130 may control the operation of the distribution unit 509 and/or the heat exchanger 508, according to the detected temperature. For example, if the temperature detected by the temperature detector 506-1 is higher than a threshold (e.g., a system default value, a value set by a user, a value adjusted automatically, etc.), the operation (e.g., the rotation speed of a fan) of the distribution unit 509 may be enhanced, and vice versa. As another example, when the temperature detected by the temperature detector 506-2 is higher than a threshold (e.g., a system default value, a value set by a user or a value adjusted automatically), the heat transfer (e.g., the flow speed of a cryogen) of the heat exchanger 508 may be increased, and vice versa. The temperature detector 506 may be a thermometer or a temperature sensor, for example, a thermistor, a resistive temperature detector, a thermocouple, a mechanical thermometer, a fiber optical thermometer, a gas thermometer, or the like, or any combination thereof.

In some embodiments, a plurality of holes or openings 504 may be arranged on one or more sides of the detector unit 502. The holes or openings 504 may allow different portions of the detector unit 502 to be exposed to the cooling medium. The sizes and/or shapes of different holes or openings 504 may be the same or different, according to various considerations including, for example, the size, shape, and/or location of the detector unit 502.

It should be noted that the above description of the diagram in FIG. 5 is merely provided for the purposes of illustration, and not intended to limit the scope of the present disclosure. For persons having ordinary skills in the art, multiple variations or modifications may be made under the teachings of the present disclosure. For example, holes or conduits may be set on a sidewall of the inner cavity to connect the inner cavity cooling medium passage 510 with other cooling medium passage outside the inner cavity. As another example, the distribution unit 509 and the heat exchanger 508 may be placed in the inner cavity. As a further example, the distribution unit 509 and the heat exchanger 508 may be placed outside the inner cavity (e.g., at the bottom of an imaging device gantry 310), and an additional passage may be configured to connect them with the inner cavity cooling medium passage 510. As a still further example, the heat exchanger 508 may be unnecessary; instead, an additional inlet may be configured to introduce a cooled cooling medium into the inner cavity, and an additional outlet may be configured to discharge heat-laden cooling medium from the inner cavity.

Figure 6:
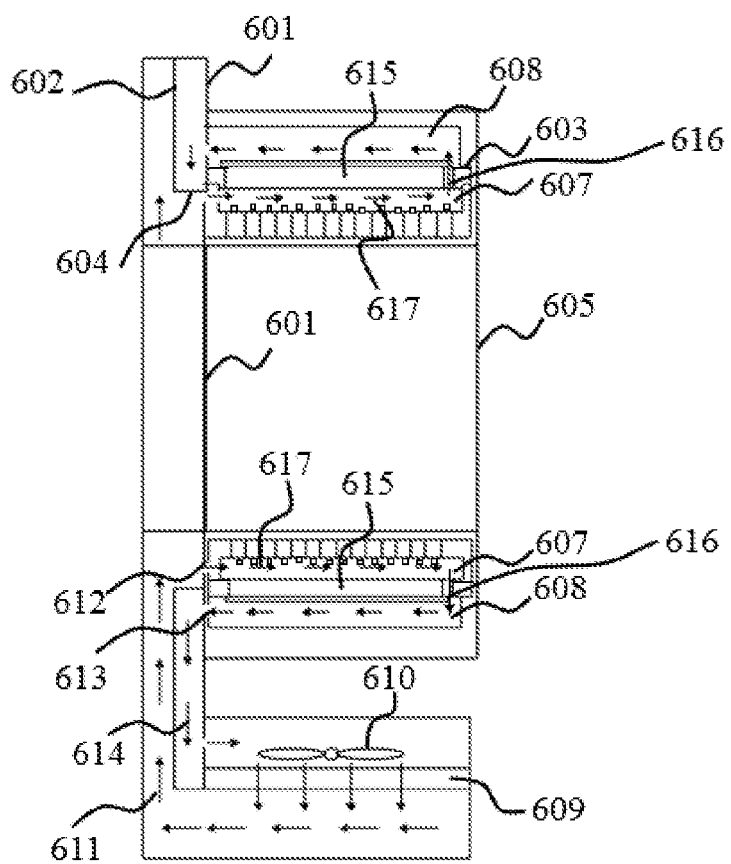
FIG. 6 is a schematic diagram illustrating an exemplary cooling medium passage according to some embodiments of the present disclosure.

FIG. 6 is a schematic diagram illustrating an exemplary cooling medium passage according to some embodiments of the present disclosure. The diagram of FIG. 6 may illustrate a section view of an imaging device gantry 310. The imaging device gantry 310 may include a shielding cover 605, a detector 603, a clapboard 601, a distribution unit 610, a heat exchanger 609, and a plurality of cooling medium passages. The shielding cover 605 may shield against an electromagnetic field and/or radiation, for example, an X-ray radiation of a CT device. In some embodiments, the shielding cover 605 may protect the detector 603 from electromagnetic interferences. The arrows illustrated in the diagram may indicate the cooling medium passages. The cooling medium passages may form at least part of a closed loop. The closed loop may be set inside the shielding cover 605. The closed loop may be in an inner cavity of the imaging device gantry 310. The distribution unit 610 may drive the cooling medium in the cooling medium passages to spread and/or circulate in the cavity. The distribution unit 610 may regulate the flow rate of the cooling medium. The distribution unit 610 may be a driver and/or a mover. For example, when a gaseous cooling medium is used, the distribution unit 610 may be a fan or a blower. In some embodiments, a flow rate of the cooling medium may be regulated through the variation of the rotation speed of the fan or the blower. The heat exchanger 609 may cool the cooling medium in the inner cavity. The heat exchanger 609 may be a shell and tube heat exchanger, a pillow plate heat exchanger, a fluid heat exchanger, a dynamic scraped surface heat exchanger, a phase-change heat exchanger, or a direct contact heat exchanger, or the like, or any combination thereof. In some embodiments, the heat exchanger 609 may use a cryogen and/or a refrigerant to cool the cooling medium. For example, the heat exchanger 609 may be an evaporator; the evaporator may include conduits with a cryogen. The clapboard 601 may divide the inner cavity into two parts: one side of the clapboard 601 may be provided with a plurality of detectors 603; the other side may be provided with one or more guiding passages (e.g., an intake passage 611 and a return passage 614). In some embodiments, an imaging device gantry 310 may include a first portion and a second portion. The distribution unit 610 and/or the heat exchanger 609 may be located in the first portion. The second portion may refer to a portion including a detector 603. The cooling medium passage in the first portion may be referred to as a first sub-passage, while the cooling medium passage in the second portion may be referred to as a second sub-passage. The first sub-passage may include the guiding passages. The second sub-passage may include the local passages close to the detector 603. In some embodiments, at least part of the second sub-passage may be alongside the detector 603.

The detector 603 may include a detector unit (e.g., a photodetector for PET device, an X-ray detector for CT device, etc.). The detector 603 may include a hollow chamber 714 housing the detector unit. The hollow chamber 714 may further include an inlet chamber 607 and a return chamber 608. The inlet chamber 607 and the return chamber 608 may be separated by a first plate 615. The detector unit may be placed in the inlet chamber 607, or the return chamber 608. In some embodiments, the detector unit may be placed in the inlet chamber 607. In some embodiments, an electronics unit may be assembled with the detector 603 into one block, and the electronics unit may be placed in the return chamber 608. The inlet chamber 607 may include an inlet hole 612. The return chamber 608 may include an outlet hole 613. In some embodiments, the inlet hole 612 and the outlet hole 613 may be set on the clapboard 601. The inlet chamber 607 and the return chamber 608 may be connected through an internal hole (e.g., inside the hollow chamber 714 of the detector 603). For example, the cooling medium may flow from the inlet chamber 607 to the return chamber 608, as illustrated by a vertical arrow 616 between them. Besides, the inlet chamber 607 and/or the return chamber 608 may have a local passage to channel the cooling medium, as illustrated by the arrows 617 inside the hollow chamber 714. In some embodiments, when a gaseous cooling medium is used, the cooling medium in local passages may contact with the detector unit, and/or the electronics unit inside the detector 603.

The guiding passages may include an intake passage 611 and a return passage 614. The intake passage 611 may guide a cooling medium to reach the inlet chamber 607. The return passage 614 may lead the cooling medium from the inlet chamber 607 to the return chamber 608. The cooling medium may further return to the heat exchanger 508 to be cooled. The intake passage 611 and the return passage 614 may be blocked by a baffle 604 and/or a passage cover plate 602 such that the intake passage 611 and the return passage 614 are not connected or in fluid communication with each other. The intake passage 611 may be connected or in fluid communication with the inlet chamber 607 through the inlet hole 612. The return passage 614 may be connected or in fluid communication with the return chamber 608 through the outlet hole 613.

In some embodiments, the detector 603 may be the target location to be cooled. The cooling medium cooled by the heat exchanger 609 may be driven by the distribution unit 610. The cooling medium may flow into the intake passage 611, and then reach the inlet chamber 607 through the inlet hole 612. Then the cooling medium may absorb heat from the inlet chamber 607, and reach the return chamber 608. The cooling medium may further absorb heat from the return chamber 608, and then flow out of the return chamber 608 through the outlet hole 613, and reach the return passage 614. The heat-laden cooling medium may flow within the return passage 614 and get to the heat exchanger 609 to be cooled.

In some embodiments, a plurality of temperature detectors (not shown) may be set in the inner cavity. The temperature detectors may be placed at any location of the imaging device gantry 310, for example, including the intake passage 611, the return passage 614, the inlet chamber 607 and/or the return chamber 608. For example, a temperature detector may be placed near the detector 603 to monitor the temperature around the detector 603. As another example, a temperature detector may be placed near the heat exchanger 609 to monitor the temperature of the cooling medium after cooling. The detected temperature may be recorded by the temperature control module 210, or the control module 130 of an imaging system 110, as shown in FIGS. 1 and 2. The temperature control module 210 may control the operation of the distribution unit 610 and/or the heat exchanger 609, according to the detected temperature. For example, when the temperature of the detector 603 is higher than a threshold (e.g., a system default value, a value set by a user, a value adjusted automatically, etc.), the operation (e.g., the rotation speed of a fan) of the distribution unit 610 may be enhanced, and vice versa. As another example, when the temperature of the heat exchanger 609 is higher than a threshold (e.g., a system default value, or a value set by a user), the heat transfer (e.g., the flow speed of a cryogen) of the heat exchanger 609 may be increased, and vice versa. The temperature detector may be a thermometer or a temperature sensor, for example, a thermistor, a resistive temperature detector, a thermocouple, a mechanical thermometer, a fiber optical thermometer, a gas thermometer, or the like, or any combination thereof.

It should be noted that the above description of the diagram in FIG. 6 is merely provided for the purposes of illustration, and not intended to limit the scope of the present disclosure. For persons having ordinary skills in the art, multiple variations or modifications may be made under the teachings of the present disclosure. For example, holes or conduits may be set on a sidewall of the inner cavity to connect the passages with other cooling medium passage outside the inner cavity. As another example, the distribution unit 610 and the heat exchanger 609 may be placed in the inner cavity. As another example, the distribution unit 610 and the heat exchanger 609 may be placed outside the inner cavity (e.g., at the bottom of an imaging device gantry 310), and an additional passage may be configured to connect with the passage inside the inner cavity. As a further example, the heat exchanger 609 may be unnecessary; instead, an additional inlet may be configured to introduce a cooled cooling medium into the inner cavity, and an additional outlet may be configured to discharge heat-laden cooling medium from the inner cavity. As a still further example, the intake passage 611 and/or the return passage 614 may be blocked by the clapboard 601, the passage cover plate 602, and/or the baffle 604. As a still further example, the intake passage 611 and/or the return passage 614 may be blocked by other clapboards, plates, and/or baffles (not shown) which may achieve similar function.

FIG. 7A through FIG. 7E illustrate exemplary arrangements of a detector and the corresponding cooling medium passage according to some embodiments of the present disclosure. In some embodiments, an imaging device may include a first portion and a second portion. The second portion may refer to the portion containing a detector unit. The cooling medium passage in the first portion (not shown) may be referred to as a first sub-passage (not shown). The cooling medium passage in the second portion may be referred to as a second sub-passage 713. The structure of the detector unit illustrated in FIG. 7A through FIG. 7E may illustrate the second portion of an imaging device, and the second sub-passage 713 may be located alongside the detector unit.

Figure 7A:
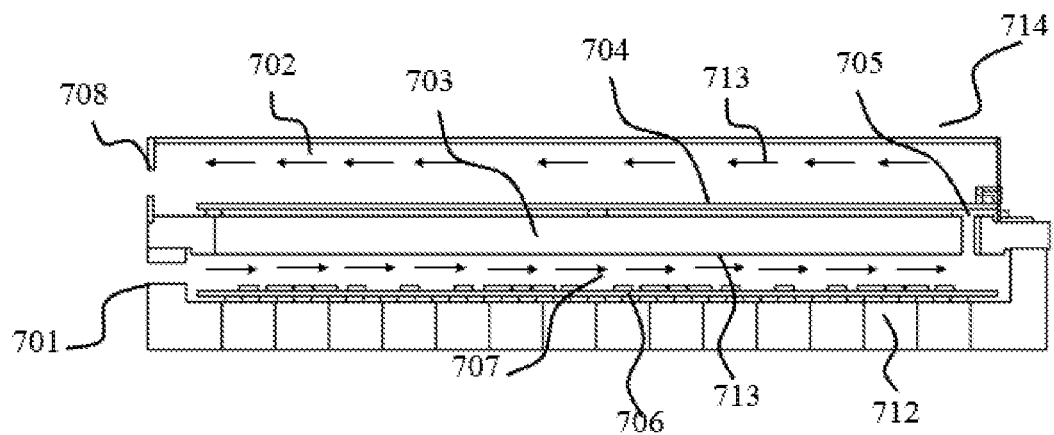
FIG. 7A through FIG. 7E illustrate exemplary arrangements of a detector and the corresponding cooling medium passage according to some embodiments of the present disclosure.
Figure 7B:
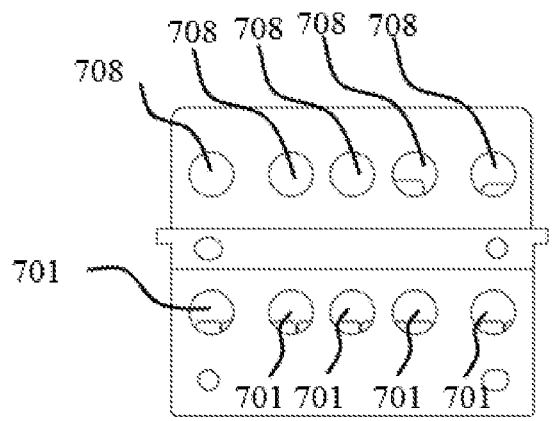

FIG. 7A and FIG. 7B illustrate an exemplary arrangement of a detector and the corresponding cooling medium passage according to some embodiments of the present disclosure. FIG. 7A provides a front view of the arrangement, and FIG. 7B provides a side view of the arrangement. The detector may include a hollow chamber 714, a detector unit 712, and an electronics unit 704. The detector unit 712 may be installed or fixed on an internal wall of the detector. The detector unit 712 may include a frontend electronics 706 to collect electrical signals. For a PET device, the detector unit 712 may include a scintillator and a photodetector. The hollow chamber 714 may include a first hole 701 and a second hole 708. The first hole 701 and the second hole 708 may be located on the same sidewall or different sidewalls of the detector. The first hole 701 may allow a cooling medium to enter the hollow chamber 714. The second hole 708 may allow the cooling medium to flow out of the hollow chamber 714.

The detector may have a first plate 703 to divide the hollow chamber 714 into two chambers: an inlet chamber 707, and a return chamber 702. The detector unit 712 may be placed in the inlet chamber 707, while the electronics unit 704 may be placed in the return chamber 702. In some embodiments, the electronics unit 704 may be installed, or fixed on the first plate 703, or elsewhere in the return chamber 702. In some embodiments, when a gaseous cooling medium is used, the cooling medium may contact with the detector unit 712 and/or the electronics unit 704.

The first hole 701 may be open to the inlet chamber 707. The second hole 708 may be open to the return chamber 702. The inlet chamber 707 and the return chamber 702 may be connected through a third hole 705. For example, a cooling medium from the outside of the detector may reach the inlet chamber 707 through the first hole 701, and cool the detector unit 712. Then the cooling medium may flow through the third hole 705 and reach the return chamber 702, and cool the electronics unit 704. The heat-laden cooling medium may exit the return chamber 702 via the second hole 708 and get to the outside of the detector. In some embodiments, the third hole 705 may be located on the first plate 703. In some embodiments, the first hole 701 and the second hole 708 may be placed on the same sidewall of the detector, and the third hole 705 may be located at a position away from the first hole 701 and the second hole 708. For example, the third hole 705 may be located on the first plate 703 near the opposite sidewall of the detector compared to the first hole 701 and the second hole 708. Thus, the cooling medium may reach most part of the inlet chamber 707 and the return chamber 702, and cool the detector unit 712 and/or the electronics unit 704.

The detector shown in FIG. 7A and FIG. 7B may be further installed or fixed within a first portion of the imaging device. The cooling medium passages of the detector may be connected to a first sub-passage (not shown) through holes or conduits located on the first portion (not shown) and/or the second portion. For example, the detector may be installed on the clapboard 601 (as illustrated in FIG. 6), the first hole 701 may be open to the inlet hole 612 (as illustrated in FIG. 6), and the second hole 708 may be open to the outlet hole 613 (as illustrated in FIG. 6). In some embodiments, the first hole 701 and the second hole 708 may be located on the sidewall of the detector. The sidewall of the detector may have a complete opening, which means the sidewall may not exist, and the first hole 701 and the second hole 708 may be integrated into one larger hole. One side of the first plate 703 may be fixed to or otherwise contact the clapboard 601 (as illustrated in FIG. 6). Thus, the inlet chamber 707 may be connected with the intake passage 611 through the inlet hole 612 located on the clapboard 601 (as illustrated in FIG. 6). The return chamber 702 may be connected with the return passage 614 through the outlet hole 613.

Figure 7C:
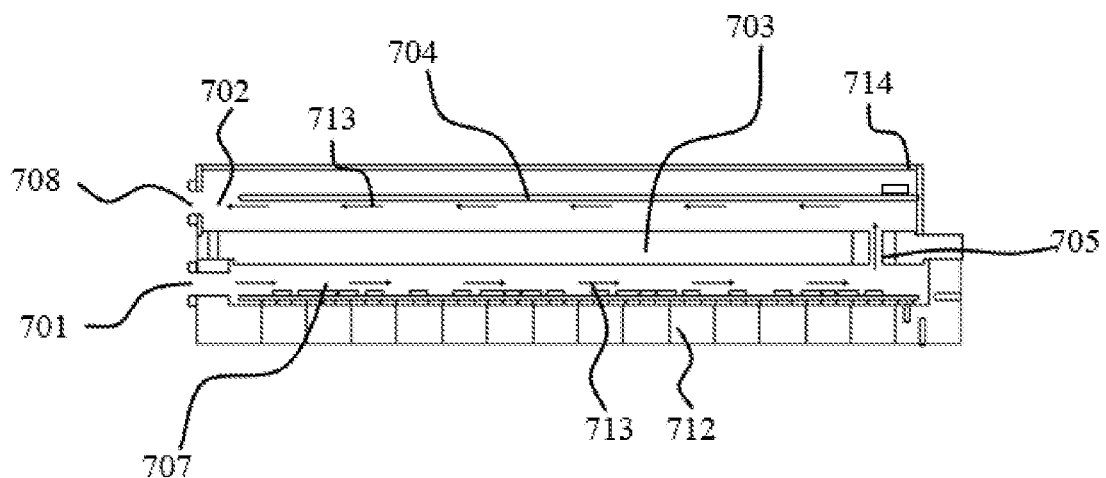

FIG. 7C illustrates an exemplary arrangement of a detector and the corresponding cooling medium passage according to some embodiments of the present disclosure. Similar to the detector shown in FIG. 7A and FIG. 7B, the detector in FIG. 7C may include a hollow chamber 714, a detector unit 712, and an electronics unit 704. In some embodiments, the detector may have a shielding cover. The hollow chamber 714 may have a first hole 701 and a second hole 708. The first hole 701 and the second hole 708 may be located on the same sidewall or different sidewalls of the detector. The first hole 701 may allow a cooling medium to enter the hollow chamber 714, while the second hole 708 may allow the cooling medium to exit the hollow chamber 714. The detector may have a first plate 703 to divide the hollow chamber 714 into two chambers: an inlet chamber 707, and a return chamber 702. The inlet chamber 707 may connect with the first hole 701. The return chamber 702 may connect with the second hole 708. The inlet chamber 707 and the return chamber 702 may be connected through a third hole 705 set on the first plate 703. The inlet chamber 707 and the return chamber 702 may include local cooling medium passages, as illustrated by the arrows. The detector unit 712 may be placed in the inlet chamber 707. The detector unit 712 may be installed or fixed on an internal wall of the detector. The electronics unit 704 may be placed in the return chamber 702. One end of the electronics unit 704 may be installed or fixed on an internal wall of the detector through a connecting piece (not shown); while the other end of the electronics unit 704 may not contact with the detector. Two ends of the electronics unit 704 in FIG. 7A may be installed or fixed, while only one end of the electronics unit 704 in FIG. 7C may be installed or fixed.

The detector shown in FIG. 7C may be further installed or fixed with the first portion of the imaging device. The cooling medium passages of the detector may be connected to a first sub-passage (not shown) through holes or conduits located in the first portion (not shown) and/or the second portion. In some embodiments, the detector may be in the shape of approximately a cuboid. The first hole 701 and the second hole 708 may be located on one of the sidewall of the detector. The sidewall may be associated with the clapboard 601 (as illustrated in FIG. 6). The first hole 701 may be connected with the inlet hole 612 (as illustrated in FIG. 6). The second hole 708 may be connected with the outlet hole 613 (as illustrated in FIG. 6). The end of the electronics unit 704 may contact or connect the clapboard 601 (as illustrated in FIG. 6) through a connecting piece. Thus, the cooling medium from the intake passage 611 may pass through the inlet hole 612 (as illustrated in FIG. 6), the first hole 701, the inlet chamber 707, the third hole 705, the return chamber 702, the second hole 708, and the outlet hole 613, and then flow into the return passage 614. As most areas of the electronics unit 704 may be in an overhanging state, most areas of the electronics unit 704 may be exposed to the cooling medium in the return chamber 702, and the cooling area may be increased. Thus, the cooling efficiency of the electronics unit 704 may be increased.

Figure 7D:
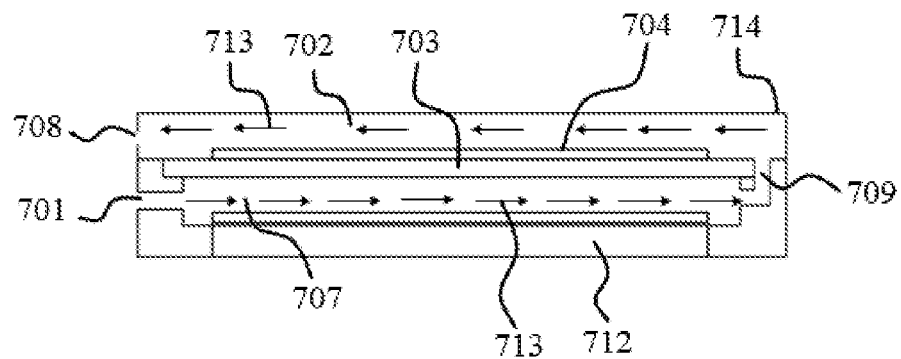

FIG. 7D illustrates an exemplary arrangement of a detector and the corresponding cooling medium passage according to some embodiments of the present disclosure. Similar to the detector shown in FIG. 7A and FIG. 7B, the detector in FIG. 7D may include a hollow chamber 714, a detector unit 712, and an electronics unit 704. In some embodiments, the detector may have a shielding cover. The hollow chamber 714 may have a first hole 701, and a second hole 708. The first hole 701 and the second hole 708 may be set on the same sidewall or different sidewalls of the detector. The first hole 701 may allow a cooling medium spread within the hollow chamber 714, while the second hole 708 may lead the cooling medium to flow out of the hollow chamber 714. The detector may have a first plate 703 to divide the hollow chamber 714 into two chambers: an inlet chamber 707, and a return chamber 702. One end of the first plate 703 may be fixed on an internal wall of the detector. For example, one end of the first plate 703 may be fixed at a position between the first hole 701 and the second hole 708. The other end of the first plate 703 may not contact any of the internal walls of the detector, which means there may be a gap between the first plate 703 and the detector. The inlet chamber 707 may connect with the first hole 701. The return chamber 702 may connect with the second hole 708. The gap between the first plate 703 and the detector may form a first internal passage 709. The inlet chamber 707 and the return chamber 702 may be connected through the first internal passage 709. The inlet chamber 707 and the return chamber 702 may include local cooling medium passages (not shown). The detector unit 712 may be placed in the inlet chamber 707. The detector unit 712 may be installed or fixed on an internal wall of the detector. The electronics unit 704 may be placed in the return chamber 702. The electronics unit 704 may be installed or fixed on the first plate 703.

The detector shown in FIG. 7D may be further installed or fixed with a first portion of an imaging device, and the cooling medium passages of the detector may be connected to a first sub-passage (not shown) through holes or conduits set on the first portion (not shown) and/or the second portion. In some embodiments, the first hole 701 and the second hole 708 may be set on one of the sidewall of the detector. The sidewall may be associated with the clapboard 601 (as illustrated in FIG. 6). The first hole 701 may be connected with the inlet hole 612 (as illustrated in FIG. 6). The second hole 708 may be connected with the outlet hole 613 (as illustrated in FIG. 6). Thus, the cooling medium from the intake passage 611 (as illustrated in FIG. 6) may pass through the inlet hole 612 (as illustrated in FIG. 6), the first hole 701, the inlet chamber 707, the first internal passage 709, the return chamber 702, the second hole 708, and the outlet hole 613, and flow into the return passage 614.

Figure 7E:
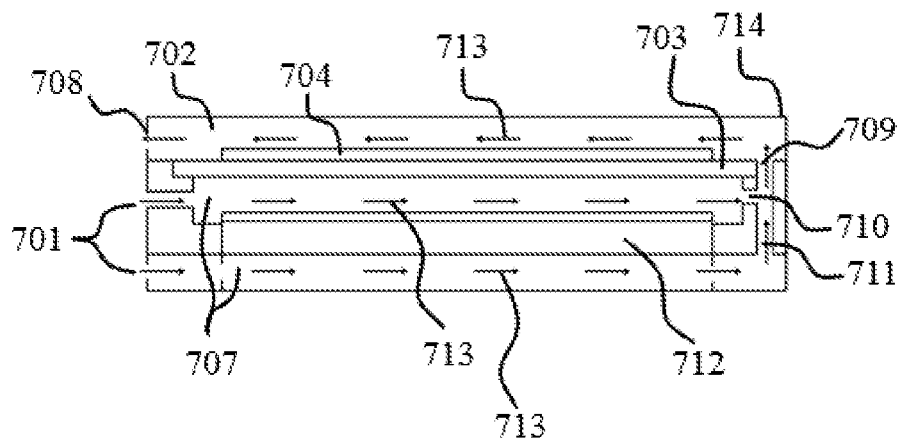

FIG. 7E illustrates an exemplary arrangement of a detector and the corresponding cooling medium passage according to some embodiments of the present disclosure. Similar to the detector shown in FIG. 7A and FIG. 7B, the detector in FIG. 7E may include a hollow chamber 714, a detector unit 712, and an electronics unit 704. In some embodiments, the detector may have a shielding cover. The hollow chamber 714 may have two first holes 701, the upper first hole and the lower first hole. The hollow chamber 714 may also have a second hole 708. The first holes 701 and the second hole 708 may be set on the same sidewall or different sidewalls of the detector. The first holes 701 may allow a cooling medium to spread within the hollow chamber 714, while the second hole 708 may lead the cooling medium to flow out of the hollow chamber 714. The detector may have a first plate 703 to divide the hollow chamber 714 into two chambers: an inlet chamber 707, and a return chamber 702. One end of the first plate 703 may be fixed on an internal wall of the detector. For example, one end of the first plate 703 may be fixed at a position between the first holes 701 and the second hole 708. The other end of the first plate 703 may not contact any of the internal walls of the detector, which means there may be a gap between the first plate 703 and the detector. The gap between the first plate 703 and the detector may form a first internal passage 709. One end of the detector unit 712 may be installed or fixed on an internal wall of the detector. For example, one end of the detector unit 712 may be fixed at a position between the first holes 701. The other end of the detector unit 712 may not contact any of the internal walls of the detector, which means there may be a gap between the detector unit 712 and the detector. The gap between the detector unit 712 and the detector may form a second internal passage 711. In some embodiments, the detector unit 712 may divide the inlet chamber 707 into two inlet chambers 707, the upper inlet chamber and the lower inlet chamber. Besides, the unfixed end of the detector unit 712 and the unfixed end of the first plate 703 may be not connected, and leave a gap between the unfixed ends of the two. The gap may form a third internal passage 710. The inlet chambers 707 may connect with the first holes 701 correspondingly. For example, the upper inlet chamber may connect with the upper first hole, and the lower inlet chamber may connect with the lower first hole. The return chamber 702 may connect with the second hole 708. The upper inlet chamber and return chamber 702 may be connected through the third internal passage 710 and the first internal passage 709. The lower inlet chamber and the return chamber 702 may be connected through the second internal passage 711 and the first internal passage 709. The inlet chambers 707 and the return chamber 702 may include local cooling medium passages, as illustrated by the arrows. The electronics unit 704 may be placed in the return chamber 702. The electronics unit 704 may be installed or fixed on the first plate 703.

The detector shown in FIG. 7E may be further installed or fixed with a first portion of an imaging device, and the cooling medium passages of the detector may be connected to a first sub-passage (not shown) through holes or conduits set on the first portion (not shown) and/or the second portion. In some embodiments, the first holes 701 and the second hole 708 may be set on one of the sidewall of the detector. The sidewall may be associated with the clapboard 601 (as illustrated in FIG. 6). As the detector may have two first holes 710, the clapboard 601 may have two inlet holes 612 correspondingly. The relative positions of the two inlet holes 612 may be matched with that of the two first holes 701. The second hole 708 may be connected with the outlet hole 613 (as illustrated in FIG. 6). Thus, the cooling medium from the intake passage 611 may pass through the inlet holes 612 (as illustrated in FIG. 6), the first holes 701 (the upper first hole and the lower first hole), the inlet chambers 707 (the upper inlet chamber and the lower inlet chamber), the third internal passage 710 (and the second internal passage 711), the first internal passage 709, the return chamber 702, the second hole 708, and the outlet hole 613, and flow into the return passage 614. The structure of the upper inlet chamber and the lower inlet chamber may increase the cooling area of the detector unit 712. Thus, the cooling efficiency of the detector unit 712 may be increased, and the service life of the detector unit 712 may be prolonged.

It should be noted that the above description of the diagram in FIG. 7 is merely provided for the purposes of illustration, and not intended to limit the scope of the present disclosure. For persons having ordinary skills in the art, multiple variations or modifications may be made under the teachings of the present disclosure. For example, the electronics unit 704 is not placed in the detector. As another example, a combination of two or more structures illustrated in FIG. 7A through FIG. 7E may be realized.

Figure 8A:
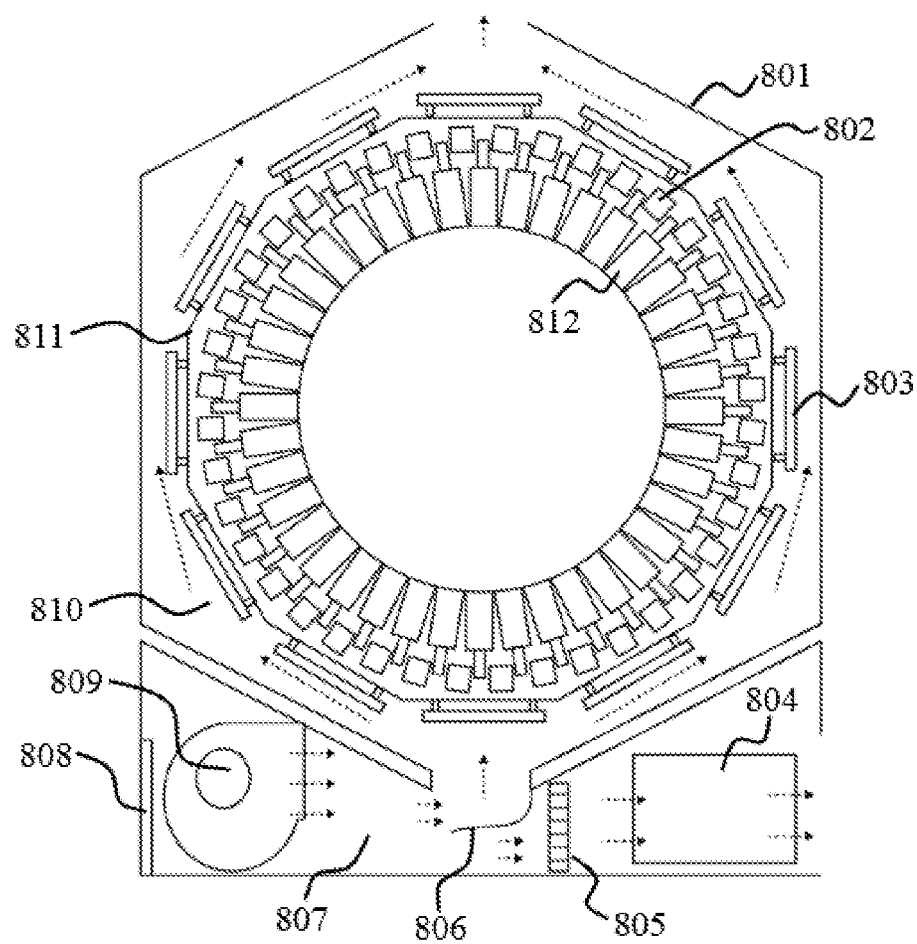
FIGS. 8A and 8B illustrate exemplary cooling module configurations of a PET system according to some embodiments of the present disclosure.
Figure 8B:
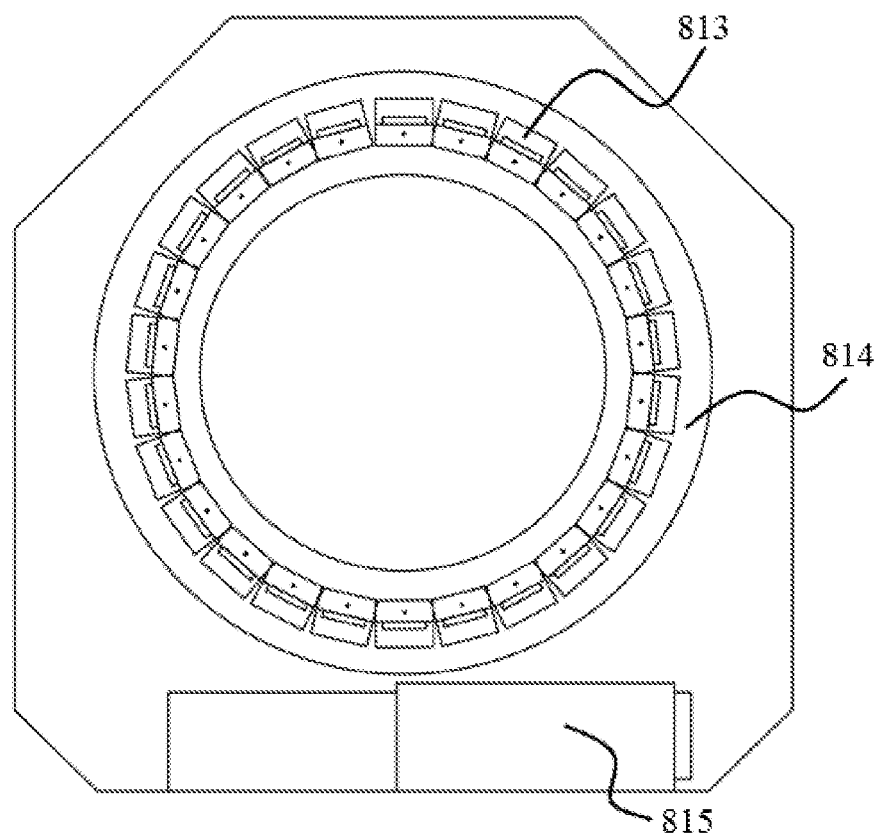

FIGS. 8A and 8B illustrate exemplary cooling module configurations of a PET system according to some embodiments of the present disclosure. FIG. 8A illustrate an exemplary configuration of a cooling module of a PET system according to some embodiments of the present disclosure. A PET system 801 may include a peripheral electronics unit 803, a detector unit 812, and a bottom electronics unit 804. The PET system 801 may further include a cooling system. The cooling system may include a closed loop cooling medium passage and an open loop cooling medium passage. In some embodiments, the closed loop cooling medium passage may cool the detector unit 812 as illustrated in FIG. 5. In some embodiments, the closed loop cooling medium passage may be further used for cooling the electronics unit as illustrated in FIG. 6 and FIGS. 7A through 7E.

The open loop cooling medium passage may include a peripheral cooling medium passage 810 and a bottom cooling medium passage 807. The PET system may include a PET ring. In some embodiments, the PET ring may include multiple detector units. The PET ring may be divided into sections by a clapboard structure 811. Different sections of the PET ring may be cooled by the closed loop cooling medium passage and the peripheral cooling medium passage 810, respectively. The clapboard structure 811 may be a clapboard and/or multiple clapboards forming an integrated structure. The peripheral cooling medium passage 810 may cool the peripheral electronics unit 803. For example, referring to FIG. 5, the peripheral cooling medium passage 511 may be located near the electronics unit 501. The peripheral electronics unit 803 may be placed on the clapboard structure 811. The bottom cooling medium passage 807 may cool the bottom electronics unit 804. In some embodiments, the bottom electronics unit 804 may be cooled by a cooling medium. In some embodiments, the bottom cooling medium passage 807 may be located below the closed cooling medium passage and the peripheral cooling medium passage 810.

The cooling system may further include a cooling module. The cooling module may be used to cool a heat-laden cooling medium. The cooling module may include a peripheral distribution unit 809 and/or a condenser 805. The peripheral distribution unit 809 may be configured to distribute a cooling medium to a peripheral cooling medium passage 810 and a bottom cooling medium passage 807. In some embodiments, the peripheral distribution unit 809 may be located in the bottom cooling medium passage 807. For example, the peripheral distribution unit 809 may introduce air from the ambient outside the PET system 801 to the peripheral cooling medium passage 810 and/or the bottom cooling medium passage 807. In some embodiments, air from the ambient may be filtered by a filter 808 before it reaches the peripheral distribution unit 809. The filter 808 may be inside and/or outside the PET system 801. An air deflector 806 may be placed in an open loop cooling medium passage. The air deflector 806 may be used to distribute the air between the peripheral cooling medium passage 810 and the bottom medium passage 807. For example, the deflector 806 may allow some air to flow into the peripheral cooling medium passage 810 and/or the condenser 805. The PET ring may further include a ventilation hole 802. The ventilation hole 802 may be located between the detector units 812 in the closed loop medium passage. In some embodiments, multiple ventilation holes 802 may be arranged evenly.

FIG. 8B illustrates an example of a cooling module configuration of a PET system according to some embodiments of the present disclosure. The PET system may include an examination space, a supporting structure 814, and a cooling module 815. The supporting structure 814 may include a detector unit 813. The detector unit may be cooled in a cooling medium passage, for example, that illustrated in FIG. 5 and/or FIG. 6. The cooling module 815 may include a distribution unit and a heat exchanger (e.g., illustrated as the distribution unit 610 and the heat exchanger 609 in FIG. 6). The cooling module 815 may be placed at the bottom of the PET system. The cooling medium passage may be a closed loop within the supporting structure 814 and/or the cooling module 815. For example, referring to FIG. 6, the cooling medium passages may form at least part of a closed loop within the first portion (including the cooling module 815) and the second portion (including the supporting structure 814). It should be noted that the above description of FIGS. 8A and 8B is merely provided for the purposes of illustration, and not intended to limit the scope of the present disclosure. For persons having ordinary skills in the art, multiple variations or modifications may be made under the teachings of the present disclosure.

Figure 9:
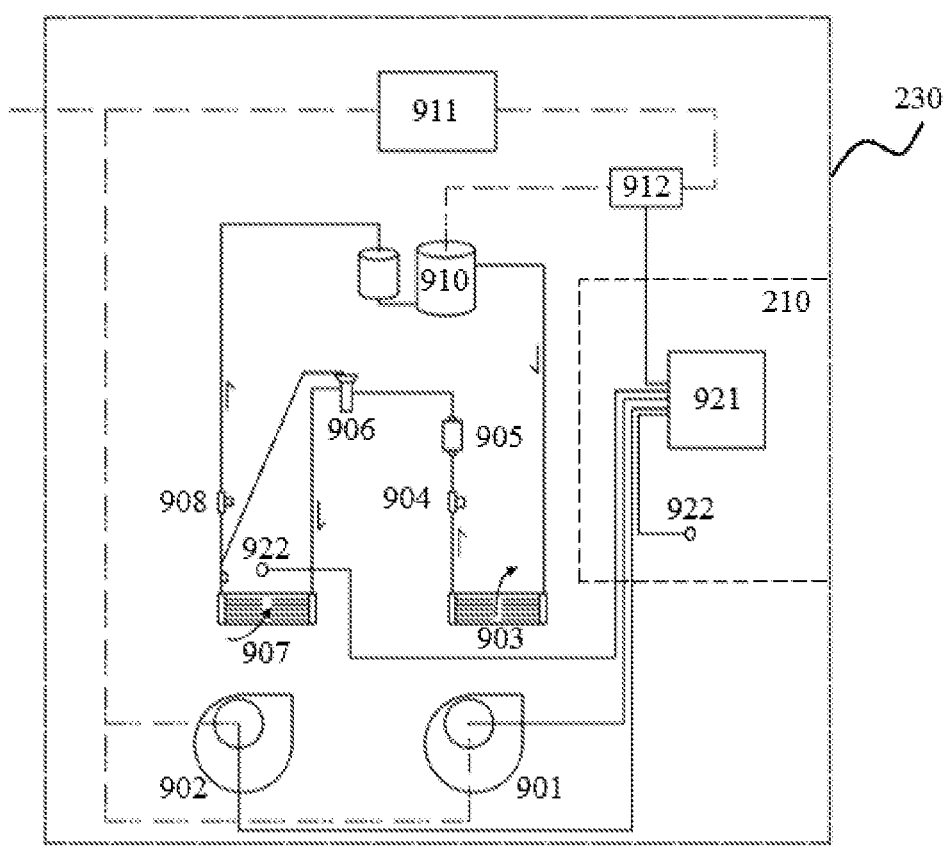
FIG. 9 illustrates an exemplary cooling module configuration of an imaging system according to some embodiments of the present disclosure.

FIG. 9 is a schematic diagram illustrating an exemplary cooling module configuration of an imaging system according to some embodiments of the present disclosure. The cooling module may provide cooling to the detector unit(s) and the electronics unit(s). As shown in FIG. 9, the cooling module 230 may include an internal fan 901, an external fan 902, a condenser 903, an expansion valve 906, an evaporator 907, a compressor 910, a power supply 911, and a driver 912. The power supply 911 may be electrically connected and provide power to different components including, for example, a fan, a driver, a compressor, a sensor, a controller, or the like, or any combination thereof. The electrical connection between the components may be a serial connection, a parallel connection, or the like, or any combination thereof. In some embodiments, the power supply 911 may be electrically connected to the driver 912 and the compressor 910 in series. In some embodiments, the power supply 911 may be electrically connected to the external fan 902 and the internal fan 901 in parallel. The driver 912 may drive one or more components including, for example, a compressor, a temperature controller, and/or a temperature sensor. In some embodiments, the driver 912, powered by the power supply 911, may drive the compressor 910. The internal fan 901 may be used in an internal closed chamber. The internal closed chamber may include at least one cooling medium passage. The cooling medium passage may form at least part of a closed loop. For example, referring to FIG. 5, the distribution unit 509, in the form of an internal fan, may facilitate the circulation of the cooling medium within the cooling medium passage 510 in the internal closed chamber. The external fan 902 may be used in an external open chamber. For example, as illustrated in FIG. 8A, the distribution unit 809 may be used in the external open chamber of the imaging system as the external fan.

The compressor 910 may increase the pressure of a refrigerant (e.g., a gaseous refrigerant). The compressor 910 may be operably connected to one or more of the condenser 903, and the evaporator 907. The expansion valve 906 may be connected to a high pressure inlet 904. In some embodiments, the evaporator 907 may be connected to the expansion valve 906 by a capillary (not shown in FIG. 9). The capillary may be used to control a pressure difference between the condenser 903 and the evaporator 907. The pressure and/or state of a refrigerant may be changed in the capillary. The evaporator 907 may be open to a low pressure inlet 908. The high pressure inlet 904 and the low pressure inlet 908 may be used for the refrigerant injection. In some embodiments, the compressor 910, the condenser 903, the expansion valve 906, the high pressure inlet 904, the evaporator 907, and the low pressure inlet 908 may be configured as a circuit loop. For example, the compressor 910 may transport the gaseous refrigerant to the condenser 903. In some embodiments, the condenser 903 may be placed near the external fan 901 (e.g., illustrated as the condenser 805 near the peripheral distribution unit 809 in FIG. 8). The condenser 903 may be use dot condense the refrigerant. By way of condensation, the refrigerant may change its state from, for example, its gaseous state to its liquid state. For example, referring to FIG. 8A, the condenser 805 may be placed in the bottom cooling medium passage 807; the gaseous refrigerant may be condensed to a liquid in the condenser 805. In some embodiments, the liquid refrigerant may be transported to the expansion valve 906. The expansion valve 906 may convert the liquid refrigerant to a mist. The expansion valve 906 may further transport the misty refrigerant to the evaporator 907. In some embodiments, the evaporator 907 may be placed near the internal fan 902.

For example, referring to FIG. 5, the heat exchanger 508 may be an evaporator located in the cooling medium passage 510 with the internal distribution unit 509. In the evaporator 907 (or the heat exchanger 508), the misty refrigerant may be converted to a gaseous refrigerant by absorbing heat from, for example, a heat-laden cooling medium, etc. The gaseous refrigerant exiting the evaporator 907 may flow to the compressor 910. In some embodiments, the refrigerant may be recycled as described above.

The cooling module 230 may further include a temperature control module 210. The temperature control module 210 may include a temperature controller 921 and a temperature sensor 922. In some embodiments, the temperature sensor 922 may include a temperature probe. The temperature probe may be an immersion probe, a contacting probe, a non-contacting probe, or the like, or any combination thereof. In some embodiments, the temperature control module 210 may include at least two temperature sensors 922. The temperature sensor 922 may measure temperature of different components and/or portions of the imaging system 100. In some embodiments, the temperature sensor 922 may measure the temperature of the evaporator 907. In some embodiments, the temperature sensor 922 may measure the temperature in the cooling medium passage 220. For example, referring to FIG. 5, the temperature sensor 506 may measure the temperature of the cooling medium passage 510. In some embodiments, one or more temperature sensors may be arranged within the cooling medium passage 510, and another temperature sensor 506 may be located near the evaporator 508.

The result of temperature measurement may further be fed to the temperature controller 921. In some embodiments, the temperature controller 921 may be electrically connected to the driver 912, the external fan 902, the internal fan 901 and the temperature sensor 922 respectively. The temperature controller 921 may control the temperature by controlling a flow rate of the cooling medium. In some embodiments, the temperature controller 921 may control the rotational speed of the compressor 910. For example, the temperature controller 921 may send a control signal to the driver 912, and then the rotational speed of the compressor 910 may be regulated. In some embodiments, the temperature controller 921 may control the power of a fan. For example, referring to FIG. 8A, the temperature controller 921 may control the external distribution unit 809 in order to adjust the flow rate of the cooling medium. For example, referring to FIG. 9, the operating of the internal fan 901 and the operation of the external fan 902 may be controlled by the temperature controller 921. In some embodiments, the temperature controller 921 may generate a control signal when the measurement result of temperature sensor 922 changed suddenly. For instance, if the temperature sensor 922 may detect that, within a period, the temperature measured at a location within the imaging system 100 has increased by a value higher than a threshold, or decreased by a value lower than a threshold, the imaging system 100 may work in an unstable or undesirable condition; the temperature controller 921 may generate a control signal in response.

The cooling module 230 may further include a filter 905. For instance, the filter 905 may be a dry filter. The filter 905 may remove an undesired matter not belonging to the refrigerant. Exemplary undesired matter may include moisture, impurities, and so on. In some embodiments, the filter 905 may be placed between the high pressure inlet 904 and the expansion 906. In some embodiments, the filter 905 may further store a certain amount of the refrigerant. In some embodiments, the refrigerants stored may be used while the volume of the refrigerant in the cooling module 230 is lower than a threshold, or when a higher cooling capacity is needed.

The examples set forth above are provided to give those of ordinary skill in the art a complete disclosure and description of how to make and use the embodiments of the arrangements, devices, compositions, systems and methods of the disclosure, and are not intended to limit the scope of what the inventors regard as their disclosure. All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which include been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by preferred embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein include the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations that is not specifically disclosed herein.

A number of embodiments of the disclosure include been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

What is claimed is:
1. An imaging system comprising:
a control module;
an imaging device including a first portion and a second portion; and
a cooling system comprising
a cooling module configured to generate a cooling medium; and a cooling medium passage configured to spread the cooling medium, the cooling medium passage belonging to a closed loop, wherein at least part of the cooling system is located within the imaging device such that the cooling medium is in direct contact with at least one target location of the imaging device, the cooling medium passage includes an intake guiding passage and a return guiding passage, the intake guiding passage being configured to guide the cooling medium to the at least one target location, the return guiding passage being configured to guide the cooling medium away from the at least one target location, the intake guiding passage and the return guiding passage sharing at least one common baffle, and wherein the imaging device includes a plurality of detector units and a plurality of electronics units, the cooling system further includes a plurality of hollow chambers, and each of the plurality of hollow chambers houses one or more of the plurality of detector units and one or more of the plurality of electronics units.

2. The imaging system of claim 1, wherein the cooling medium passage further includes a sub-passage, the intake guiding passage and the return guiding passage are located within the first portion, and the sub-passage is located within the second portion.

3. The imaging system of claim 2, wherein at least part of the intake guiding passage and the return guiding passage is configured to form a fluid communication between the first portion and the second portion.

4. The imaging system of claim 2, wherein the second portion comprises a detector unit.

5. The imaging system of claim 4, wherein at least a portion of the detector unit is located within the second sub-passage.

6. The imaging system of claim 5, wherein the cooling medium contacts the detector unit.

7. The imaging system of claim 4, wherein the second portion further comprises an electronics unit.

8. The imaging system of claim 7, wherein at least a portion of the detector unit and the electronics unit are located within the sub-passage.

9. The imaging system of claim 7, wherein the cooling medium contacts the detector unit and the electronics unit.

10. The imaging system of claim 7, wherein the second portion further includes a first plate, and the first plate divides the second portion into a first chamber and a second chamber in fluid communication with the first chamber.

11. The imaging system of claim 10, wherein the first plate and the detector unit divide the second portion into three chambers.

12. The imaging system of claim 1, wherein the cooling system further comprises a temperature control module.

13. The imaging system of claim 12, wherein the temperature control module comprises a temperature detector.

14. The imaging system of claim 1, wherein the cooling module comprises a fan and a heat exchanger.

15. The imaging system of claim 1, wherein the imaging device is a Positron Emission Tomography (PET) device.

16. The imaging system of claim 1, wherein the cooling system further comprises a peripheral cooling medium passage.

17. The imaging system of claim 1, wherein the at least one common baffle is airtight.

18. The imaging system of claim 1, wherein the at least one target location is located outside the intake guiding passage and the return guiding passage.

19. The imaging system of claim 1, wherein at least one of the plurality of hollower chambers includes a plate, the plate being configured to divide the at least one hollower chamber into an inlet chamber and a return chamber, the inlet chamber and the return chamber being configured to function as part of the cooling medium passage and channel the cooling medium.

* * * * *